(12) United States Patent
Chheda et al.

(10) Patent No.: US 10,138,218 B2
(45) Date of Patent: Nov. 27, 2018

(54) PROCESS FOR PREPARING FURFURAL FROM BIOMASS

(71) Applicant: SHELL OIL COMPANY, Houston, TX (US)

(72) Inventors: Juben Nemchand Chheda, Houston, TX (US); Paul Richard Weider, Houston, TX (US); Robert Lawrence Blackbourn, Houston, TX (US); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 32 days.

(21) Appl. No.: 15/502,897

(22) PCT Filed: Aug. 13, 2015

(86) PCT No.: PCT/US2015/044981
§ 371 (c)(1),
(2) Date: Feb. 9, 2017

(87) PCT Pub. No.: WO2016/025673
PCT Pub. Date: Feb. 18, 2016

(65) Prior Publication Data
US 2017/0226076 A1    Aug. 10, 2017

Related U.S. Application Data

(60) Provisional application No. 62/037,195, filed on Aug. 14, 2014.

(51) Int. Cl.
*C07D 307/50*    (2006.01)

(52) U.S. Cl.
CPC .................. *C07D 307/50* (2013.01)

(58) Field of Classification Search
CPC ................................... C07D 307/50
See application file for complete search history.

(56) References Cited

U.S. PATENT DOCUMENTS

| | | |
|---|---|---|
| 2,078,241 A | 4/1937 | Fulmer et al. |
| 2,536,732 A | 1/1951 | Dunlop |
| 3,549,319 A | 12/1970 | Wilson et al. |
| 4,409,032 A | 10/1983 | Paszner et al. |
| 4,461,648 A | 7/1984 | Foody |
| 4,533,743 A | 8/1985 | Medeiros et al. |
| 5,536,325 A | 7/1996 | Brink |
| 5,789,210 A | 8/1998 | Ho et al. |
| 5,820,687 A | 10/1998 | Farone et al. |
| 6,475,768 B1 | 11/2002 | Otero et al. |
| 7,741,084 B2 | 6/2010 | Viitanen et al. |
| 7,741,119 B2 | 6/2010 | Viitanen et al. |
| 7,781,191 B2 | 8/2010 | Dunson, Jr. et al. |
| 8,168,807 B2 | 5/2012 | Wabnitz et al. |
| 8,466,242 B2 | 6/2013 | Geremia et al. |
| 2003/0162271 A1 | 8/2003 | Zhang et al. |
| 2009/0061490 A1 | 3/2009 | Edwards et al. |
| 2010/0019191 A1 | 1/2010 | Hoffer et al. |
| 2010/0312028 A1 | 12/2010 | Olson et al. |
| 2012/0107887 A1 | 5/2012 | Chheda et al. |
| 2012/0122152 A1 | 5/2012 | Blackbourn et al. |
| 2012/0157697 A1 | 6/2012 | Burket et al. |
| 2012/0302765 A1 | 11/2012 | Dumesic et al. |
| 2013/0196400 A1 | 8/2013 | Weider et al. |
| 2013/0295629 A1 | 11/2013 | Weider et al. |
| 2014/0018555 A1 | 1/2014 | DeVries et al. |
| 2014/0107355 A1 | 4/2014 | Dumesic et al. |
| 2017/0240518 A1* | 8/2017 | Chheda ............... C07D 307/50 |

FOREIGN PATENT DOCUMENTS

| | | |
|---|---|---|
| EP | 1863901 | 12/2007 |
| EP | 1727890 | 5/2008 |
| WO | 9500518 | 1/1995 |
| WO | 9513362 | 5/1995 |
| WO | 9701113 | 1/1997 |
| WO | 2006096130 | 9/2006 |
| WO | 2007009463 | 1/2007 |

(Continued)

OTHER PUBLICATIONS

Galbe, et al.; "A review of the production of ethanol from softwood"; Appl. Microbiol. Biotechnol.; vol. 59; pp. 618-628; 2002.
Holtzapple, et al.; The Ammonia Freeze Explosion (AFEX) Process; Applied Biochemistry and Biotechnology; vol. 28/29; pp. 59-74; 1991.
Kumar, et al.; "Methods for Pretreatment of Lignocellulosic Biomass for Efficient Hydrolysis and Biofuel Production"; Ind. Eng. Chem. Res.; vol. 48; pp. 3713-3729; 2009.
Lavarack, et al.; "The acid hydrolysis of sugarcane bagasse hemicellulose to produce xylose, arabinose, glucose and other products"; Biomass and Bioenergy; vol. 23; pp. 367-380; 2002.

(Continued)

*Primary Examiner* — Andrew D Kosar
*Assistant Examiner* — John S Kenyon

(57) ABSTRACT

Furfural is produced from biomass material containing pentosan, in high yields, in a production process comprising treating the biomass with a solution containing at least one α-hydroxysulfonic acid thereby hydrolyzing the biomass to produce a product stream containing at least one $C_5$-carbohydrate compound in monomeric and/or oligomeric form, and dehydrating the $C_5$-carbohydrate compound in the presence of a heterogeneous solid acid catalyst, in a biphasic reaction medium comprising an aqueous phase and a water-immiscible organic phase, at a temperature in the range of from about 100° C. to about 250° C. to produce a dehydration product stream containing furfural. An aqueous stream is separated from the dehydration product, which can be optionally recycled to the hydrolysis step.

20 Claims, 1 Drawing Sheet

(56) References Cited

FOREIGN PATENT DOCUMENTS

| WO | 2007028811 | 3/2007 |
| WO | 2007136762 | 11/2007 |
| WO | 2008119082 | 10/2008 |
| WO | 2009109631 | 9/2009 |

OTHER PUBLICATIONS

Möller; "Outputs from the EPOBIO project"; published by CPL Press, Tall Gables, The Sydings Speen, Newbury, Berks RG14 TRZ UK; 2006.

Mosier, et al.; "Features of promising technologies for pretreatment of lignocellulosic biomass"; Bioresource Technology; vol. 96; pp. 673-686; 2005.

Ong; "Conversion of Lignocellulosic Biomass to Fuel Ethanol-A Brief Review"; The Planter; vol. 80, No. 941; pp. 517-524; 2004.

Yang et al.; One-Step Catalytic Transformation of Carbohydrates and Cellulosic Biomass to 2,5 Dimethyltetrahydrofuran for Liquid Fuels; ChemSusChem; vol. 3; pp. 597-603; 2010.

Brown et al.; "Fast Pyrolysis and Bio-Oil Upgrading"; Biomass-to-Diesel Workshop; Pacific Northweat national Laboratory, Richland, Washington; Sep. 5-6, 2006.

International Search Report for PCT/US2015/044981 dated Sep. 28, 2015; 3 pages.

\* cited by examiner

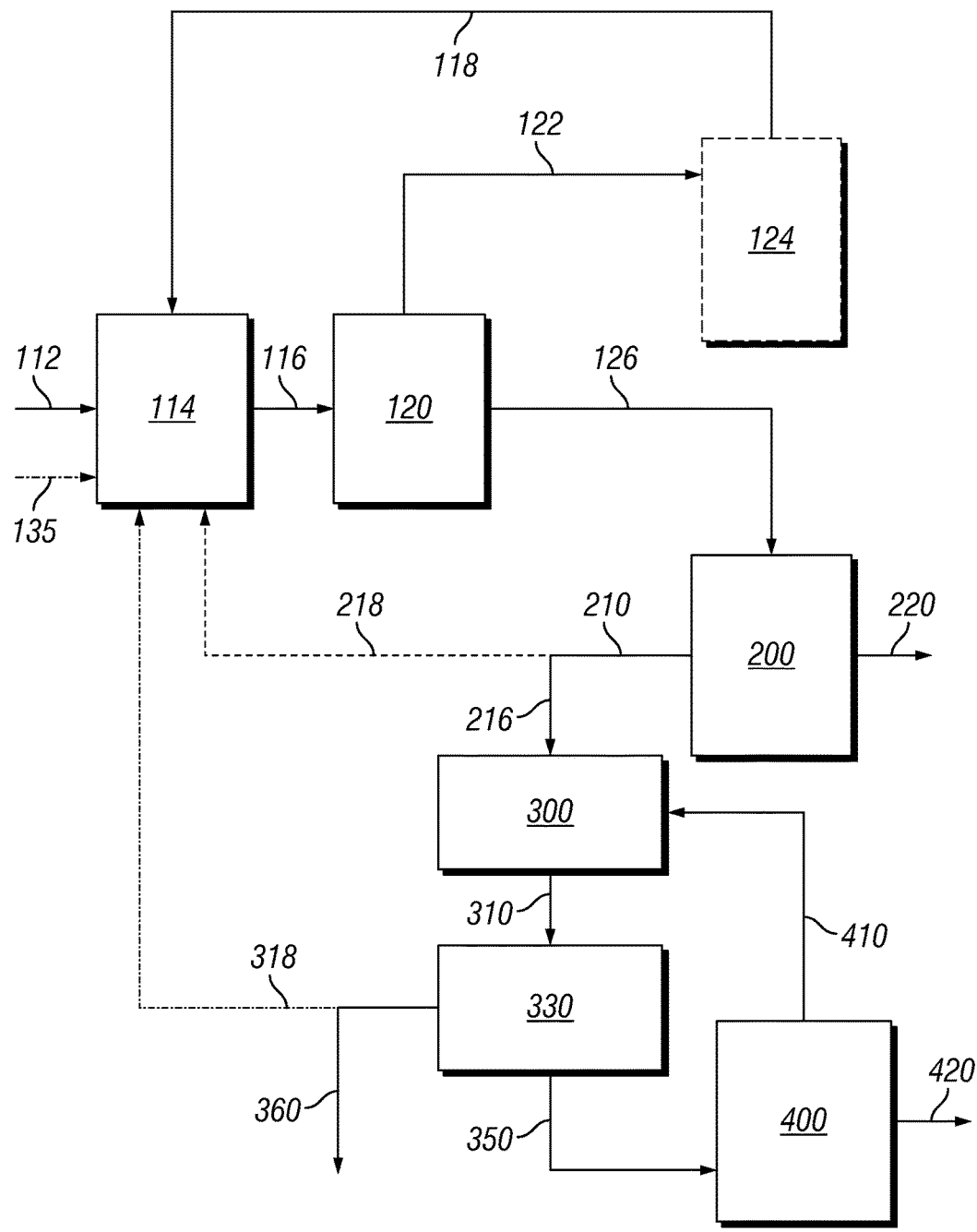

PROCESS FOR PREPARING FURFURAL FROM BIOMASS

PRIORITY CLAIM

The present application is the National Stage (§ 371) of International Application No. PCT/US2015/044981, filed Aug. 13, 2015, which claims priority from U.S. Provisional Application No. 62/037195, filed Aug. 14, 2014 incorporated herein by reference.

FIELD OF THE INVENTION

The invention relates to a process for preparing furfural from biomass, and more specifically to a treatment of biomass and production of furfural from materials containing polysaccharides and/or lignocelluloses.

BACKGROUND OF THE INVENTION

Lignocellulosic biomass is viewed as an abundant renewable resource for chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. These structural components are comprised primarily of pentose and hexose sugars monomers. Cellulose is a polymer comprised mostly of condensation polymerized glucose and hemicellulose is a precursor to pentose sugars, mostly xylose. These sugars can be converted into valuable components, provided they can be liberated from the cell walls and polymers that contain them. However, plant cell walls have evolved considerable resistance to microbial, mechanical or chemical breakdown to yield component sugars. In order to overcome recalcitrance ground biomass is altered by a chemical process known as pretreatment. The aim of the pretreatment is to hydrolyze the hemicellulose, break down the protective lignin structure and disrupt the crystalline structure of cellulose. All of these steps enhance enzymatic accessibility to the cellulose during the subsequent hydrolysis (saccharification) step.

The original approaches dating back to the early 19th century involve complete chemical hydrolysis using concentrated mineral acids such as hydrochloric acid, nitric, or sulfuric acid. Numerous improvements to these processes have been made earning higher sugar yields from the biomass feedstock. These higher acid concentration approaches provide higher yields of sugars, but due to economic and environmental reasons the acids must be recovered. The primary obstacle to practicing this form of saccharification has been the challenges associated with recovery of the acid [M. Galbe and G. Zacchi, Appl. Microbiol. Biotechnol. Vol. 59, pp. 618-628 (2002)]. Recent efforts toward separating sulfuric acid and sugars using ion resin separation or hydrochloric acid and sugars via an amine extraction process and subsequent thermal regeneration of the acid have been described in U.S. Pat. No. 5,820,687. However, both of these approaches are cumbersome and expensive in practice.

Dilute acid processes have also been attempted to perform chemical saccharification and one such example is the Scholler-Tornesch Process. However usage of dilute acid requires higher temperatures and this usually results in low yields of the desired sugars due to thermal degradation of the monosaccharides. Numerous approaches of this type have been made in the past and all have failed to meet economic hurdles. [See, for example, Lim Koon Ong, "Conversion of Lignocellulosic Biomass to Fuel Ethanol—A Brief Review," The Planter, Vol. 80, No. 941, August 2004, and, "Cell Wall Saccharification," Ralf Moller, in Outputs from the EPOBIO Project, 2006; Published by CPL Press, Tall Gables, The Sydings, Speen, Newbury, Berks RG14 1RZ, UK].

The saccharification of the cellulose enzymatically holds promise of greater yields of sugars under milder conditions and is therefore considered by many to be more economically attractive. The recalcitrance of the raw biomass to enzymatic hydrolysis necessitates a pretreatment to enhance the susceptibility of the cellulose to hydrolytic enzymes. A number of pretreatment methods, such as described by Mosier, et al. [Bioresource Technology, Vol. 96, pp. 673-686 (2005)], have been developed to alter the structural and chemical composition of biomass to improve enzymatic conversion. Such methods include treatment with a dilute acid steam explosion, as described in U.S. Pat. No. 4,461,648, hydrothermal pretreatment without the addition of chemicals as described in WO 2007/009463 A2, ammonia freeze explosion process as described by Holtzapple, M. T., et al. [Applied Biochemistry and Biotechnology, 28/29, pp. 59-74], and an organosolve extraction process described in U.S. Pat. No. 4,409,032. Despite these approaches, such pretreatment has been cited as the most expensive process in biomass-to-fuels conversion [Ind. Eng. Chem. Res., Vol. 48(8), 3713-3729.(2009)].

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that enzymatic Saccharification is successful. The parameters which can be employed to control the conditions of the pretreatment are time, temperature, and acid loading. These are often combined in a mathematical equation termed the combined severity factor. In general, the higher the acid loading employed, the lower the temperature that can be employed; this comes at a cost of acid and its need to recycle the acid. Conversely, the lower the temperature, the longer the pretreatment process takes; this comes at the cost of productivity. However the use of the higher concentrations of acid required to lower the pretreatment temperatures below that where furfural formation becomes facile [B. P. Lavarack, et al., Biomass and Bioenergy, Vol. 23, pp. 367-380 (2002)] once again requires the recovery of the strong acid. If dilute acid streams and higher temperatures are employed the pretreatment reaction the acid passing downstream to the enzymatic hydrolysis and subsequent fermentation steps must be neutralized resulting in inorganic salts which complicates downstream processing and requires more expensive waste water treatment systems. This also results in increased chemical costs for acid and base consumption.

More recently, in US20120122152, α-hydroxysulfonic acids have been shown to be effective in the pretreatment and hydrolysis of biomass with the additional benefit of being recoverable and recyclable through reversal to the acids primary components (aldehyde, $SO_2$ and water). This pretreatment process has been shown to provide numerous benefits compared to dilute mineral acid pretreatment. However, at the low temperature, the formation of furfural is low.

A method for preparing furfural may use a batch process based on a Quaker Oats technology developed in 1920 using sulfuric acid. The batch process is known to be significantly inefficient. That is, the theoretical furfural yield is about 30 to 40%, the residence time in the reactor is significant long as 4.5 to 5.5 hours, water of 50 MT per 1 MT of furfural is consumed, and a significant amount of harmful substance is included in effluents. In addition, costs consumed for working are considerably increased Further, whether batch or continuous, when using such acid catalyst, the process corrosion and the acid wastes are generated, such that it is difficult to separate, recover, and recycle a non-reactive raw material and the acid catalyst. Further, the economic efficiency of the process may be very vulnerable according to the increase in investment costs of process facility and low product yield and environmental toxicity, recovery, and recycle may be complicated even in the process of using an organic solvent

SUMMARY OF THE INVENTION

The inventions disclosed and taught herein are directed to methods for the synthesis of furfural and similar organic materials from a biomass feedstock in high yields that optionally allows for easier recycle.

In an embodiment of the present invention, a method is provided for producing furfural from biomass material containing pentosan:
(a) providing a biomass containing pentosan;
(b) contacting the biomass with a solution containing at least one α-hydroxysulfonic acid thereby hydrolyzing the biomass to produce a product stream containing at least one $C_5$-carbohydrate compound in monomeric and/or oligomeric form, and α-hydroxysulfonic acid;
(c) separating at least a portion of the α-hydroxysulfonic acid from the product stream containing at least one $C_5$-carbohydrate compound to provide an acid-removed product stream containing the at least one $C_5$-carbohydrate compound and recovering the α-hydroxysulfonic acid in its component form;
(d) separating a liquid stream containing said at least one $C_5$-carbohydrate compound and a wet solid stream containing remaining biomass from the acid-removed product;
(e) dehydrating the $C_5$-carbohydrate compound in at least a first portion of the liquid stream in the presence of a heterogenous solid acid catalyst, in a biphasic reaction medium comprising an aqueous phase and a water-immiscible organic phase, at a temperature in the range of from about 100° C. to about 250° C.;
(f) separating an organic phase stream containing furfural and an aqueous stream from the dehydration product stream;
(g) recycling at least a portion of the aqueous stream or a second portion of the liquid stream to step (b);
(h) recovering furfural from the organic phase stream.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

The FIGURE schematically illustrates a block flow diagram of an embodiment of the furfural production process of the invention from biomass.

DETAILED DESCRIPTION OF THE INVENTION

It has been found that the present invention provides an improved method for the production of furfural from biomass in a batch, continuous or semi-continuous manner, (optionally as a closed-loop process). By use of the α-hydroxysulfonic acid, the acid can be readily separated by heating or reducing pressure and recycled, and only require a fraction of an acid and fraction of a time compared to conventional process to dehydrate the $C_5$-carbohydrate compound, thus increasing efficiency and decreasing complications. By use of the α-hydroxysulfonic acid for pretreatment of biomass to produce a liquid stream containing $C_5$-carbohydrate compound, it is possible to use a solid acid catalyst for subsequent dehydration of the $C_5$-carbohydrate compound, increasing efficiency and decreasing complications in the system. Further, by separating a liquid stream containing $C_5$-carbohydrate compound from the wet solids from the product stream from the α-hydroxysulfonic acid pretreatment step, it has been found that furfural can be produced without excessive degradation of C6 sugars in the subsequent dehydration step. For example, the controlled return of the aqueous stream following the dehydration of the C5 carbohydrates extracted from the biomass allows for maintaining an optimized reaction process flow. Additionally, the method allows for increased amounts of both C5-carbohydrate and C6-carbohydrate-containing intermediate product streams to be efficiently separated and recovered and sent on to further upgrading and/or purification steps (dehydration, fermentation, etc), whereas often these intermediate products are lost or destroyed during treatment steps. Furthermore, the process methods allow for higher concentrations of pentosan-comprising biomass to be treated, which increased the product concentration, thereby reducing the size of equipment and facilitating the recovery of valuable intermediates and products overall. In addition, the use of extraction methods within the process allows for recovery of the desired product (furfural) without having to distill or strip much water with it (as azeotrope). When carried out in situ, for example during dehydration, it reduces the formation of undesired by products such as humins and/or impurities and thereby increase yield of desired product. Further, in an embodiment where the aqueous stream is recycled to the hydrolysis step, such recycle of the aqueous stream may be partial.

In a preferred embodiment, it has further been found that by titrating the α-hydroxysulfonic acid salt with strong acid and then reverting the α-hydroxysulfonic acid as its primary components, the acid components can be recovered virtually quantitatively providing for a cost reduction in the reversible acid pretreatment process. When α-hydroxysulfonic acid encounters a basic species, such as a carbonate, the anionic salt form of the acid is generated. This acid salt is not reversible as the α-hydroxysulfonic acid must be in the protonic form to revert to primary components. Since biomass is always accompanied by caustic inorganic materials, we have found that the formation of the anion salt of α-hydroxysulfonic acid represent the largest "loss" of the α-hydroxysulfonic acid in the potential reversible acid pretreatment process. It has been further found that a small amount of a mineral acid can conveniently be used to also titrate the α-hydroxysulfonic acid salt and enhance recovery of the α-hydroxysulfonic acid by reverting its salt to the acid form and then recovering the α-hydroxysulfonic acid in its primary components. If the α-hydroxysulfonic acid cannot be recycled, it is expensive relative to mineral acids. Thus, by recovering the α-hydroxysulfonic acid from its acid salt, provides for a cost reduction in the treatment process.

The α-hydroxysulfonic acid is effective for treatment of biomass hydrolyzing the biomass to fermentable sugars like pentose such as xylose at lower temperature, (e.g., about 100° C. for α-hydroxymethane sulfonic acid or α-hydroxyethane sulfonic acid) producing little furfural in the process. A portion of the cellulose has also been shown to hydrolyze under these comparatively mild conditions. Other polysaccharides such as starch are also readily hydrolyzed to component sugars by α-hydroxysulfonic acids. Further, the α-hydroxysulfonic acid is reversible to readily removable and recyclable materials unlike mineral acids such as sulfuric, phosphoric, or hydrochloric acid. The lower temperatures and pressures employed in the biomass treatment leads to lower equipment cost. The ability to recycle fragile pentose sugars from the end of pretreatment to the inlet of pretreatment, without their subsequent conversion to undesirable materials such as furfural, allows lower consistencies in the pretreatment reaction itself, yet still passing a high consistency solids mixture containing high soluble sugars out of pretreatment. Biomass pretreated in this manner has been shown to be highly susceptible to additional saccharification, especially enzyme mediated saccharification.

The α-hydroxysulfonic acids have the general formula $$\underset{R_1R_2CSO_3H}{\overset{OH}{|}}$$

wherein $R_1$ and $R_2$ are individually hydrogen or hydrocarbyl with up to about 9 carbon atoms that may or may not contain oxygen can be used in the treatment of the instant invention. The alpha-hydroxysulfonic acid can be a mixture of the aforementioned acids. The acid can generally be prepared by reacting at least one carbonyl compound or precursor of carbonyl compound (e.g., trioxane and paraformaldehyde) with sulfur dioxide or precursor of sulfur dioxide (e.g., sulfur and oxidant, or sulfur trioxide and reducing agent) and water according to the following general equation 1.

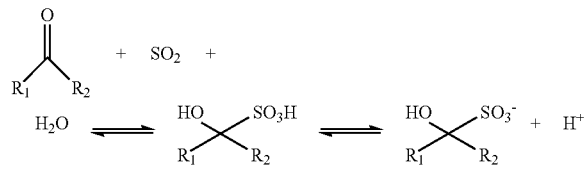

where $R_1$ and $R_2$ are individually hydrogen or hydrocarbyl with up to about 9 carbon atoms or a mixture thereof.

Illustrative examples of carbonyl compounds useful to prepare the alpha-hydroxysulfonic acids used in this invention are found where
$R_1=R_2=H$ (formaldehyde)
$R_1=H, R_2=CH_3$ (acetaldehyde)
$R_1=H, R_2=CH_2CH_3$ (propionaldehyde)
$R_1=H, R_2=CH_2CH_2CH_3$ (n-butyraldehyde)$R_1=H, R_2=CH(CH_3)_2$ (i-butyraldehyde)
$R_1=H, R_2=CH_2OH$ (glycolaldehyde)
$R_1=H, R_2=CHOHCH_2OH$ (glyceraldehdye)
$R1=H, R2=C(=O)H$ (glyoxal)

$R_1 = H, R_2 =$ 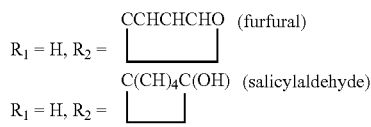 CCHCHCHO (furfural)

C(CH)₄C(OH) (salicylaldehyde)

$R_1 = H, R_2 =$ 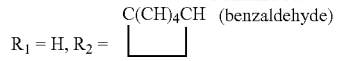 C(CH)₄CH (benzaldehyde)

$R_1=R_2=CH_3$ (acetone)
$R_1=CH_2OH, R_2=CH_3$ (acetol)
$R_1=CH_3, R_2=CH_2CH_3$ (methyl ethyl ketone)
$R_1=CH_3, R_2=CHC(CH_3)_2$ (mesityl oxide)
$R_1=CH_3, R_2=CH_2CH(CH_3)_2$ (methyl i-butyl ketone)
$R_1, R_2=(CH_2)_5$ (cyclohexanone) or
$R_1=CH_3, R_2=CH_2Cl$ (chloroacetone)

The carbonyl compounds and its precursors can be a mixture of compounds described above. For example, the mixture can be a carbonyl compound or a precursor such as, for example, trioxane which is known to thermally revert to formaldehyde at elevated temperatures, metaldehdye which is known to thermally revert to acetaldehyde at elevated temperatures, or an alcohol that maybe converted to the aldehyde by dehydrogenation of the alcohol to an aldehyde by any known methods. An example of such a conversion to aldehyde from alcohol is described below. An example of a source of carbonyl compounds maybe a mixture of hydroxyacetaldehyde and other aldehydes and ketones produced from fast pyrolysis oil such as described in "Fast Pyrolysis and Bio-oil Upgrading, Biomass-to-Diesel Workshop", Pacific Northwest National Laboratory, Richland, Wash., Sep. 5-6, 2006. The carbonyl compounds and its precursors can also be a mixture of ketones and/or aldehydes with or without alcohols that may be converted to ketones and/or aldehydes, preferably in the range of 1 to 7 carbon atoms.

The preparation of α-hydroxysulfonic acids by the combination of an organic carbonyl compounds, $SO_2$ and water is a general reaction and is illustrated in equation 2 for acetone.

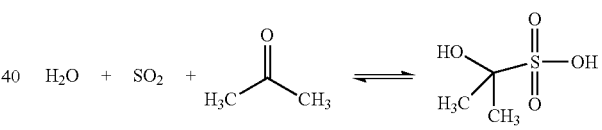

The α-hydroxysulfonic acids appear to be as strong as, if not stronger than, HCl since an aqueous solution of the adduct has been reported to react with NaCl freeing the weaker acid, HCl (see U.S. Pat. No. 3,549,319).

The reaction in equation 1 is a true equilibrium, which results in facile reversibility of the acid. That is, when heated, the equilibrium shifts towards the starting carbonyl, sulfur dioxide, and water (component form). If the volatile components (e.g. sulfur dioxide) is allowed to depart the reaction mixture via vaporization or other methods, the acid reaction completely reverses and the solution becomes effectively neutral. Thus, by increasing the temperature and/or lowering the pressure, the sulfur dioxide can be driven off and the reaction completely reverses due to Le Châteliers principle, the fate of the carbonyl compound is dependant upon the nature of the material employed. If the carbonyl is also volatile (e.g. acetaldehyde), this material is also easily removed in the vapor phase. Carbonyl compounds such as benzaldehyde, which are sparingly soluble in water, can form a second organic phase and be separated by mechanical means. Thus, the carbonyl can be removed by conventional means, e.g., continued application of heat and/or vacuum, steam and nitrogen stripping, solvent washing, centrifugation, etc. Therefore, the formation of these acids is reversible in that as the temperature is raised, the sulfur dioxide and/or aldehyde and/or ketone can be flashed from the mixture and condensed or absorbed elsewhere in order to be recycled. These reversible acids, which are approximately as strong as strong mineral acids, are effective in biomass treatment reactions.

Since the acids are effectively removed from the reaction mixture following treatment, neutralization with base to complicate downstream processing is substantially avoided. The ability to reverse and recycle these acids also allows the use of higher concentrations than would otherwise be economically or environmentally practical. As a direct result, the temperature employed in biomass treatment can be reduced to diminish the formation of byproducts such as furfural or hydroxymethylfurfural.

It has been found that the position of the equilibrium given in equation 1 at any given temperature and pressure is highly influenced by the nature of the carbonyl compound employed, steric and electronic effects having a strong influence on the thermal stability of the acid. More steric bulk around the carbonyl tending to favor a lower thermal stability of the acid form. Thus, one can tune the strength of the acid and the temperature of facile decomposition by the selection of the appropriate carbonyl compound.

In one embodiment, the acetaldehyde starting material to produce the alpha-hydroxysulfonic acids can be provided by converting ethanol, produced from the fermentation of the treated biomass of the invention process, to acetaldehyde by dehydrogenation or oxidation. Such processes are described in US20130196400 which disclosure is herein incorporated by reference in its entirety.

As used herein, the term "biomass" means organic materials produced by plants (e.g., leaves, roots, seeds and stalks). Common sources of biomass include: agricultural wastes (e.g., corn stalks, straw, seed hulls, sugarcane leavings, bagasse, nutshells, and manure from cattle, poultry, and hogs); wood materials (e.g., wood or bark, sawdust, timber slash, and mill scrap); municipal waste (e.g., waste paper and yard clippings); and energy crops (e.g., poplars, willows, switch grass, alfalfa, prairie bluestream, corn, soybean, algae and seaweed). The term "biomass" also refers to the primary building blocks of all the above, including, but not limited to, saccharides, lignins, celluloses, hemicelluloses, and starches. The term "polysaccharides" refers to polymeric carbohydrate structures, of repeating units (either mono- or di-saccharides) joined together by glycosidic bonds. These structures are often linear, but may contain various degrees of branching.

Examples include storage polysaccharides such as starch and glycogen, and structural polysaccharides such as cellulose and chitin.

As used herein the term "pentosan" refers to a polysaccharide containing C5 carbohydrate monomeric unit.

As used herein, the term "carbohydrate" is defined as a compound that consists only of carbon, hydrogen, and oxygen atoms, wherein the ratio of carbon atoms, hydrogen atoms, to oxygen atoms when converted to monomeric sugars upon hydrolysis is 1:2:1. Well known examples of carbohydrates include sugars and sugar-derived oligomers and sugar-derived polymers. The term "C5 carbohydrate(s)" refers to any carbohydrate, without limitation, that has five (5) carbon atoms in its monomeric unit. The definition includes pentose sugars of any description and stereoisomerism (e.g., D/L aldopentoses and D/L ketopentoses). C5 carbohydrates can include (by way of example and not limitation) xylose, arabinose, lyxose, ribose, ribulose, and xylulose, in their monomeric and polymeric forms. Polymeric C5 carbonydrates can contain several C5 carbohydrate monomers and in some instances even contain some (lesser) amount of C6 carbohydrate monomers. According to the invention, the term "pentose", in addition to chemical compounds of formula C5H10O5 ring such as xylose or arabinose or mixtures thereof, may also include derivatives products including pentose and their derivatives. The term "C6 carbohydrate" refers to any carbohydrate, without limitation, that has six (6) carbon atoms in its monomeric unit. The definition includes hexose sugars of any description and stereoisomerism (e.g., D/L aldohexoses and D/L ketohexoses). C6 carbohydrates include (by way of example and not limitation) allose, altrose, fructose, galactose, glucose, gulose, idose, mannose, psicose, sorbose, tagatose, and talose, in their monomeric, oligomeric and polymeric forms. Polymeric C6 carbohydrates can contain several C6 carbohydrate monomers, and in some instances even contain some (lesser) amount of C5 carbohydrate monomers.

The term "dehydration", as used herein, refers to the removal of a water molecule from a molecule that contains at least one hydroxyl group.

As used herein, the term "humins" refers to the dark, amorphous and undesirable acid byproducts and resinous material resulting from sugar and other organic compound degradation. Humins may also be produced by acid hydrolysis of carbohydrates. Yang and Sen [Chem. Sus. Chem., Vol. 3, pp. 597-603 (2010)] report the formation of humins during production of fuels from carbohydrates such as fructose, and speculate that the humins are formed by acid-catalyzed dehydration. The molecular weight of heavy components of humins can range from 2.5 to 30 kDa.

As used herein, the term "miscible" refers to a mixture of components that, when combined, form a single phase (i.e., the mixture is "monophasic") under specified conditions (e.g., component concentrations, temperature).

As used herein, the term "immiscible" refers to a mixture of components that, when combined, form a two, or more, phases under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two immiscible liquid phases, for example, an aqueous phase and a water-immiscible organic solvent phase. The term "biphasic" can also be used to describe a method employing such a reaction medium.

The FIGURE shows an embodiment of the present invention for the improved production of furfural from biomass. In this embodiment, a biomass feedstock containing pentosan ("pentosan-containing biomass feedstock") 112 is introduced to a hydrolysis reaction system 114 along with an optional recycle stream 218 and optional recycle stream 318. The hydrolysis reaction system 114 may comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116, containing at least one C5-carbohydrate, at least one α-hydroxysulfonic acid, and optionally at least one salt of α-hydroxysulfonic acid and solids comprising lignin, cellulose and hemicellulosic material is introduced to acid removal system 120 where the α-hydroxysulfonic acid is removed in its component form, then is recovered 122 (and optionally scrubbed 124), and produces a product stream 126. The recovered acids (whether in acid form or component form) are recycled via stream 118 to the hydrolysis reaction system 114. The product stream 126 contains at least one C5-carbohydrate, optionally C6-carbohydrate, substantially without the alpha-hydroxysulfonic acids. Optionally, at least a portion of the liquid on product stream 116 containing α-hydroxysulfonic acid can be recycled to the hydrolysis reaction system 114 (not shown).

The second product stream 126 is provided to a separation system 200 where a high solids/liquid mixture ("wet solids") can be separated from the acid-removed product stream to form a wet solids stream 220 containing undissolved solids containing cellulose, and a bulk liquid stream 210 that may constitute up to 20 to 95 wt % of the liquid from the acid-removed product stream that contains C5-carbohydrates (pentose) and optionally hexose and optionally the salt of α-hydroxysulfonic acids. In one embodiment, the wet solids stream containing cellulose may further be hydrolyzed by other methods, for example by enzymes to further hydrolyze the biomass to sugar products containing hexose (e.g., glucose) and fermented to produce alcohols and acids such as disclosed in US Publication Nos. 2009/0061490, 2012/0122152, 2013/0295629, and U.S. Pat. No. 7,781,191 which disclosures are hereby incorporated by reference. In another embodiment, the wet solids stream can suitably be used to generate power by the burning of the wet solid residue e.g. in a co-generation boiler. Alternatively, the wet solid product stream may be converted and optionally dried to form pellets, which can be used to produce for instance power at remote locations.

At least a portion (a second portion) of the bulk liquid stream 210 may be optionally recycled to the hydrolysis reaction system via 218 where the bulk liquid stream comprise greater than about 2 wt %, preferably 5 wt % or greater, more preferably about 8 wt % or greater, of C5 carbohydrates and C6 Carbohydrates based on the bulk liquid stream. The bulk liquid stream is preferably recycled in such a manner as to keep the hydrolysis reaction pumpable, preferably about 20 wt % or less of solids content in the hydrolysis reactor and further accumulate the C5 carbohydrates content of the bulk liquid stream 210 through recycle. As one embodiment, a portion of the bulk liquid recycle stream 218 can be used to dilute the hydrolysis reaction system 114 towards the inlet of the biomass in the hydrolysis reactor in the system, and/or for ease of solids extraction at the reactor bottoms (or reactor system exit) or can be added to a extractor or towards the reactor product stream 116 for dilution A mineral acid 135 may be optionally introduced to 114 (or optionally added instead to 116, 120, 126, 210 or 218 which are not shown) in an amount sufficient to titrate salt of alpha-hydroxysulfonic acid if any. The alpha hydroxysulfonic acid may be optionally recovered in its component form from titration then recovered (and optionally scrubbed) that may be recycled to the hydrolysis reaction system.

The dehydration step 300 occurs in a biphasic reaction medium (contains aqueous phase and water-immiscible organic phase), the aqueous phase being that carried through from separation system 200, the organic phase being one or more organic solvents that are substantially immiscible with the aqueous phase. The use of organic solvent with preferred selectivity towards furfural extraction, extracts furfural from the aqueous phase as it is formed during the dehydration reaction. This may improve overall furfural yield. A further advantage is that by extracting the furfural into the organic phase, the undesired loss of furfural via degradation reactions happening in the aqueous phase is reduced.

Following the dehydration step 300, dehydration product stream 310 is transferred to a liquid-liquid extractor 330 for the extraction step, optionally after cooling of the stream. The extractor 330 can be operated at a temperature range from about room temperature to about the dehydration temperature, so long as the liquid separates into two liquid phases at the extractor temperature. The organic phase is separated from the aqueous phase, and thus obtained aqueous recycle stream 318 at least in part may optionally be fed directly back into the process loop at the hydrolysis reaction system 114. Depending upon the salt, and optional other organic byproduct, content of the aqueous stream, aqueous recycle stream 318 may be treated to remove unwanted or excessive amounts of salts and/or organic byproducts. Preferably, aqueous recycle stream is subjected to a separation step (not shown). The recovered aqueous recycle stream obtained after treatment of aqueous recycle stream, is reintroduced to the hydrolysis reaction system 114. Salts, and optionally other organic byproducts like humins and acetic acids, are formed as a byproduct during one or more of the process steps. Typically, part of stream 318 may also be purged 360 from the process to prevent the build-up of byproducts.

Prior to undergoing the liquid-liquid extraction step 330, dehydration product stream 310 may optionally be routed through a, preferably solid/liquid, separation step, to remove any insoluble humins or other tar that may have been formed during the dehydration step 300, and which may otherwise negatively interfere with the separation of the organic phase from the aqueous phase, or later separation or purification steps 400. The humins or tar will predominantly end up in the solid phase and will thus not, or to a lesser extent, affect the subsequent organic/aqueous separation step 330. Formation of tar, char, and/or humins is a well known problem associated with the production of bio-based products, and their non removal from the production stream can result in problems during downstream purification and/or separation steps.

The organic phase is recovered from extraction step 330 as organic product stream 350, containing the target organic compounds such as furfural, furfural derivatives (such as hydroxyl methylfurfural (HMF), methyl-furfural) and levulinic acid. Although, part of organic product stream 350 may be recycled to dehydration step (or reactor(s)) 300, the majority of organic product stream 350 is subjected to a separation step, preferably one or more distillation steps, in a recovery zone 400. If the extraction solvent is low-boiler, it will be removed as top product, eventually together with water, water/furfural azeotropic mixture and other light organic products such as acetic acid. Furfural will then be removed as bottom product of 400, optionally with other high-boiling impurities such as HMF, levulinic acid or soluble humins. If the extractive solvent is high-boiler, it will be removed as bottom product of 400 together with other high-boiling impurities. Furfural is then removed as top product, optionally with other low-boiling impurities (AA) and optionally with water, e.g. as azeotropic mixture. Both top- and bottom stream of 400 may optionally undergo further purification, e.g. by distillation, to remove undesired impurities from solvent or from furfural. Residual water from the reaction that was not removed during the liquid-liquid extraction step, and which may contain acetic acid or other low-boiling impurities, is removed from recovery zone 400, with recovery of furfural via stream 420.

Organic solvents 410 removed/recovered during the separation in recovery zone 400 may be recycled back into the process, such as by reintroduction back into the dehydration step 300 via a organic recycle stream 410, in order to minimize production costs and maintain the reaction process and process efficiency. Alternatively, at least part of the organic solvents can be directed to a further solvent purification process such as column distillation/separation or solvent-solvent extraction, prior to reintroduction back into the production process, so as to remove impurities, primarily humins (heavy byproducts), as well as purify the solvent before reintroduction (not shown). After the solvent purification step, fresh solvent may be added to the purified solvent stream or organic recycle stream 410 prior to reintroduction to the dehydration step 300 or introduced to the dehydration step 300 so as to maintain the required volume of organic phase in the dehydration step.

In another embodiment, a biomass feedstock containing pentosan ("pentosan-containing biomass feedstock") 112 is introduced to a hydrolysis reaction system 114 along with both the recycle stream 218 and an aqueous recycle stream 318.

The biomass is typically preprocessed to suitable particles size that may include grinding. Not intending to restrict the scope of the invention, it is typically found that it is easier to process smaller particles of biomass. Biomass that is size reduced to facilitate handling (e.g. less than 1.3 cm) are particularly susceptible materials.

Various factors affect the conversion of the biomass feedstock in the hydrolysis reaction. The carbonyl compound or incipient carbonyl compound (such as trioxane) with sulfur dioxide and water should be added to in an amount and under conditions effective to form alpha-hydroxysulfonic acids. The temperature and pressure of the hydrolysis reaction should be in the range to form alpha-hydroxysulfonic acids and to hydrolyze biomass into fermentable sugars. The amount of carbonyl compound or its precursor and sulfur dioxide should be to produce alpha-hydroxysulfonic acids in the range from about 1 wt %, preferably from about 5 wt %, to about 55 wt %, preferably to about 40 wt %, more preferably to about 20 wt %, based on the total solution. For the reaction, excess sulfur dioxide is not necessary, but any excess sulfur dioxide may be used to drive the equilibrium in eq. 1 to favor the acid form at elevated temperatures. The contacting conditions of the hydrolysis reaction may be conducted at temperatures preferably at least from about 50° C. depending on the alpha-hydroxysulfonic acid used, although such temperature may be as low as room temperature depending on the acid and the pressure used. The contacting condition of the hydrolysis reaction may range preferably up to and including about 150° C. depending on the alpha-hydroxysulfonic acid used. In a more preferred condition the temperature is at least from about 80° C., most preferably at least about 100° C. In a more preferred condition the temperature range up to and including about 90° C. to about 120° C. The reaction is preferably conducted at as low a pressure as possible, given the requirement of containing the excess sulfur dioxide. The reaction may also be conducted at a pressure as low as about 0.1 bara, preferably from about 3 bara, to about pressure of as high as up to 11 bara. The temperature and pressure to be optimally utilized will depend on the particular alpha-hydroxysulfonic acid chosen and optimized based on economic considerations of metallurgy and containment vessels as practiced by those skilled in the art.

Numerous methods have been utilized by those skilled in the art to circumvent these obstacles to mixing, transport and heat transfer. Thus weight percentage of biomass solids to total liquids (consistency) may be as low as 1% or higher depending on the apparatus chosen and the nature of the biomass (even as high as 33% if specialized equipment is developed or used). The solids percent is weight percent of dry solids basis and the wt % liquids contains the water in the biomass. In a preferred embodiment, where a more conventional equipment is desired, then the consistency is from at least 1 wt %, preferably at least about 2 wt %, more preferably at least about 8 wt %, up to about 25 wt %, preferably to about 20 wt %, more preferably to about 15 wt %.

The temperature of the hydrolysis reaction can be chosen so that the maximum amount of extractable carbohydrates are hydrolyzed and extracted as sugar (more preferably pentose and/or hexose) or monosaccharide from the biomass feedstock while limiting the formation of degradation products. The temperatures required for successful pretreatment are controlled by the reaction time, the pH of the solution (acid concentration), and the reaction temperature. Thus as the acid concentration is raised, the temperature may be reduced and/or the reaction time extended to accomplish the same objective. The advantages of lowering the reaction temperature are that the fragile monomeric sugars are protected from degradation to dehydrated species such as furfurals and that the lignin sheath is not dissolved or melted and re-deposited upon the biomass. If high enough levels of acid are employed, temperatures can be reduced below the point at which sugar degradation or lignin deposition are problematic; this in turn is made possible through the use of reversible α-hydroxysulfonic acids. In such a low temperature process it becomes possible to recycle a sugars mixture from the back of a pretreatment process to the front of a pretreatment process. This allows the sugars to build to a high steady state value while still handling a pumpable slurry through the pretreatment process. In this process biomass, water, and α-hydroxysulfonic acid are combined in an acid hydrolysis step and reacted to effect biomass pretreatment. The acids are separated from the reaction mixture as described above and recycled to the pretreatment reactor. Then a concentrated high solids/liquid mixture (wet solid stream) is separated from the bulk liquid, which may be recycled to the reactor as well. The aqueous phase from the dehydration step is recycled to the hydrolysis step and in this manner the biomass to liquids ratio is set by the feed ratio of these components and the optimized target of wet biomass to move into enzymatic hydrolysis and/or acid catalyzed dehydration.

In some embodiments, a plurality of reactor vessels may be used to carry out the hydrolysis reaction. These vessels may have any design capable of carrying out a hydrolysis reaction. Suitable reactor vessel designs can include, but are not limited to, batch, trickle bed, co-current, counter-current, stirred tank, down flow, or fluidized bed reactors. Staging of reactors can be employed to arrive the most economical solution. The remaining biomass feedstock solids may then be optionally separated from the liquid stream to allow more severe processing of the recalcitrant solids or pass directly within the liquid stream to further processing that may include enzymatic hydrolysis, fermentation, extraction, distillation and/or hydrogenation. In another embodiment, a series of reactor vessels may be used with an increasing temperature profile so that a desired sugar fraction is extracted in each vessel. The outlet of each vessel can then be cooled prior to combining the streams, or the streams can be individually fed to the next reaction for conversion.

Suitable reactor designs can include, but are not limited to, a backmixed reactor (e.g., a stirred tank, a bubble column, and/or a jet mixed reactor) may be employed if the viscosity and characteristics of the partially digested biobased feedstock and liquid reaction media is sufficient to operate in a regime where bio-based feedstock solids are suspended in an excess liquid phase (as opposed to a stacked pile digester). It is also conceivable that a trickle bed reactor could be employed with the biomass present as the stationary phase and a solution of α-hydroxysulfonic acid passing over the material.

In some embodiments, the reactions described below are carried out in any system of suitable design, including systems comprising continuous-flow (such as CSTR and plug flow reactors), batch, semi-batch or multi-system vessels and reactors and packed-bed flow-through reactors. For reasons strictly of economic viability, it is preferable that the invention is practiced using a continuous-flow system at steady-state equilibrium. In one advantage of the process in contrast with the dilute acids pretreatment reactions where residual acid is left in the reaction mixture (<1% wt. sulfuric acid), the lower temperatures employed using these acids (5 to 20% wt.) results in substantially lower pressures in the reactor resulting in potentially less expensive processing systems such as plastic lined reactors, duplex stainless reactors, for example, such as 2205 type reactors.

The wet solids stream 220 contains at least 5 wt % of undissolved solids containing cellulose, preferably in the range of 12 wt % to about 50 wt % undissolved solids containing cellulose, preferably in the range of 15 wt % to 35 wt % undissolved solids containing cellulose, and more preferably in the range of 20 wt % to 30 wt % undissolved solids containing cellulose, based on the wet solid product stream.

The bulk liquid stream 210 comprises carbohydrate compounds, in particular comprises C5-carbohydrates, such as pentose. The bulk liquid stream 210 may optionally comprise C6-carbohydrates such as hexose, however, the majority of the carbohydrates in the bulk liquid stream are C5-carbohydrates, i.e. bulk liquid stream 210 comprises carbohydrate compounds, of which carbohydrate compounds at least 50 wt % are C5-carbohydrate compounds, based on the total weight of the carbohydrate compounds in bulk liquid stream 210. The bulk liquid stream may comprise of up to 20 wt % to 95 wt % of the liquid contained in the digestion product stream.

At least a portion of the bulk liquid stream 216 is provided to a dehydration system 300 where the stream is passed over a solid acid dehydration catalyst under dehydration reaction conditions, with the addition of a additional solvent as appropriate. At least a portion of the bulk liquid stream may be recycled 218 to the hydrolysis reaction system 114, where the bulk liquid stream may be recycled in such a manner as to keep the hydrolysis reaction pumpable along with the aqueous recycle stream 318, preferably about 20 wt % or less of solids content in the hydrolysis reactor 114. An advantage of recycling part of the bulk liquid stream to the hydrolysis reaction system 114 is that the concentration of C5-carbohydrates in bulk liquid stream 210 can be increased while keeping the overall reaction mixture pumpable without the addition of dilution water. Required make-up water can be introduced to the process system in numerous locations as appropriate to achieve desired results.

Dehydration system 300 is a biphasic system for performing a dehydration reaction. The use of a biphasic system compared to typical aqueous commercial processes for furfural production has the advantage that improved furfural yields may be obtained due to the in-situ extraction of furfural into the organic phase. Furthermore the use of an aqueous and organic phase allows for a more efficient separation of the furfural from the aqueous phase.

Dehydration process stream 300 is then introduced to the extraction system (preferably a liquid-liquid extraction system) 330. Aqueous recycle stream 318 is at least in part recycled to hydrolysis reaction system 114. The organic product stream 350 is then introduced to a separation zone 400, preferably comprising one or more distillation units, so as to produce the desired product, furfural. Optionally, part of organic product stream 350 may be recycled to dehydration system 300. By recycling part of organic product stream to dehydration system 300, the concentration of furfural in stream 350 may be increased which is beneficial when separating the furfural form the organic solvent.

The solid acid catalyst used in the dehydration step ("dehydration acid") can be a heterogeneous solid acid catalyst as long as it can catalyze the dehydration of C5 carbohydrates to furfural and/or its derivatives. Preferred heterogeneous solid acid catalyst, may include acidic ion exchange resins, for example, such as sulfonated resins (e.g., polystyrene sulfonate), acidic zeolites, for example, such as HZSM-5 HY, HUY and HUSY zeolites (e.g., with 0.5 to 0.74 nm pore diameters) β-zeolite (e.g. Si/Al=12), H-beta (e.g., Si/Al=19), layered clays such as hydroltalcites, amorphous silica alumina, gamma alumina, mesoporous silicate and aluminosilicates such as MCM-41, aluminum incorporated mesoporous silica, for example, such as Al-MCM-41, and AL-SBA-15, sulfonic acid functionalized metal oxides such as sulfated tin oxides, and microporous silicoaluminophasphates (SAPO), perfluorinated ion-exchange materials such as Nafion® SAC-13 and Nafion-117, sulfonated grapheme oxide, and heteropolyacids. Commercial examples of acidic ion exchange resin catalysts includes, for example, DOWEX™ HCR-S, DOWEX HCR-W2, DOWEX M-31, DOWEX G-26, DOWEX DR 2013, Amberlyst™ 70 (available from Dow Chemical Co.) and Amberlyst® 15 (wet) ion-exchange resin, AMBERJET™ 1200 (H) ion exchange resin, Amberlite® IR-118 (H), Amberlite® IR-120 (plus), Amberlite 15, Amberlite® XN-1010, and Nafion® Resins (available from Signma-aldrichCo.) Commercial example of amorphous silica alumina catalyst include, for example X-600 catalyst (available from Criterion Catalysts & Technologies L.P.).

Total acid site strength of the solid acid catalyst is higher than 0.05 mmol/g, preferably higher than 0.5 mmol/gm, more preferably higher than 2 mmol/g. It can be even be higher than 10 mmol/gm as measured by $NH_3$-TPD method Preferably, the amount of acid catalyst used can be in the range of 0.05 mmol/g or 10 mmol/g of total acid sites of solid acid catalyst. Typically, the acid catalyst will be in excess of the amount necessary to convert at least 80%, preferably 90% of the xylose under conditions described below.

Since biomass may contains caustic inorganic materials (such as calcium and potassium), we have found that the formation of the anion salt of α-hydroxysulfonic acid represent the largest "loss" of the α-hydroxysulfonic acid in the reversible acid pretreatment process. When α-hydroxysulfonic acid encounters a basic species, such as a carbonate, the anionic salt form of the acid is generated. This acid salt is not reversible as the α-hydroxysulfonic acid must be in the protonic form to revert to primary components.

We have found that by titrating the α-hydroxysulfonic acid salt with strong acid and then reverting the α-hydroxysulfonic acid as its primary components, the acid components can be recovered virtually quantitatively providing for a cost reduction in the reversible acid pretreatment process. Thus if maximum recovery of the α-hydroxysulfonic acid is desired, a strong acid, such as mineral acid is optionally added in small quantity sufficient to titrate the salt.

By optionally adding about a molar equivalent amount of a mineral acid (such as for example, hydrochloric, sulfuric or phosphoric acid) to a solution of salts of α-hydroxysulfonic acids, an equilibrium can be achieved between the protonic and mineral salt versions of the acids. By the term about a molar equivalent, the molar equivalent may be ±20%.

For example, when the potassium salt of alpha-hydroxyethanesulfonic acid (HESA) is treated with an equivalent of sulfuric (a divalent acid), phosphoric (a divalent strong acid), or hydrochloric acid (a monovalent acid), the HESA can be flashed overhead as $SO_2$ and acetaldehyde leaving potassium sulfate, potassium monohydrogen phosphate, or potassium chloride in solution. When HESA is recovered overhead, the pH of the salt solution rises to what it was prior to the addition of the mineral acid.

The reaction (titration) of the α-hydroxysulfonic acid salt with strong mineral acid and then reverting the α-hydroxysulfonic acid as its primary components is illustrated in equation 3 for calcium salt of α-hydroxysulfonic acid.

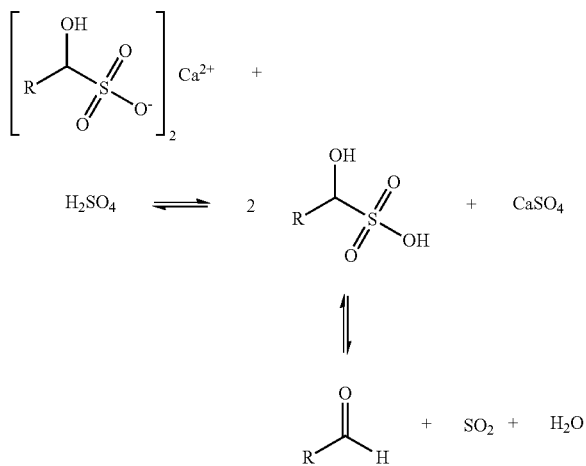

By adding about a molar equivalent amount of a mineral acid (e.g., hydrochloric, sulfuric or phosphoric acid) to a solution of salts of α-hydroxysulfonic acids, equilibrium can be achieved between the protonic and mineral salt versions of the acids. As only the α-hydroxysulfonic acid is reversible to volatile components, following Le Chatelier's principle, all of the alpha-hydroxysulfonic acid can be recovered and the salt of the mineral acid is formed.

The titration may be carried out in 300, or carried out in 114-120. For example, it may be preferable to carry out the titration in 114-120 for reduction of the amount of salt trapped in the wet solid residue 220.

The second product stream 126 is transferred to a separation system 200 (solid-liquid separator or phase separator), where the wet solids stream 220 comprising solids, and primarily solids comprising cellulose, is separated from the bulk liquid stream 210 that contains primarily C5-carbohydrate products, such as xylose. Examples of suitable separation method, for example, may include centrifugal force, filtration, decantation, and other like methods. Optionally, at least a portion of the liquid stream containing the residual α-hydroxysulfonic acid from the reaction stream 116 (carbohydrate containing product stream) may be recycled to the hydrolysis reaction system.

At least a first portion of the bulk liquid stream is subsequently provided to a dehydration step for dehydration of the C5-carbohydrates in the bulk liquid product stream, by feeding stream 216 into a reaction vessel of the dehydration step 300.

Either one or both of streams 210 or 216 may be flashed to remove part of the water (not shown) to concentrate streams 210 and/or 216. The separation step 200 may be carried out in any suitable solid/liquid separating device such as, but not limited to, filters, centrifuges, screw presses, etc. As mentioned before, the liquid stream may optionally be recycled to the hydrolysis step to build the concentration of C5-carbohydrates. Optionally, stream 216 may also be subjected to a flash, distillation or multi-effect evaporator to increase the C5-carbohydrate concentration.

The dehydration step 300 occurs in a biphasic mixture of aqueous and organic phases, the aqueous phase being that carried through from separation step 200, the organic phase being one or more organic solvents that are substantially immiscible with the aqueous phase. The use of organic solvent with preferred selectivity towards furfural extraction, extracts furfural from the aqueous phase as it is formed during the dehydration reaction. This may improve overall furfural yield. A further advantage is that by extracting the furfural into the organic phase, the undesired loss of furfural via degradation reactions happening in the aqueous phase is reduced.

The preferred organic phase for use in the present invention comprises a water-immiscible organic solvent that is substantially immiscible with the aqueous phase containing C5-carbohydrate products. Preferably such water-immiscible organic solvents have a maximum water solubility of less than about 30 wt %, preferably less than about 10 wt %, and most preferably less than about 2 wt % at ambient (room) temperature. The preferred organic solvents are 1-butanol, sec-butyl phenol (SBP), MIRK, toluene and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), cyclic alcohols (e.g., cyclohexanol), straight or branched alkanones (e.g. butanone (i.e., methylethyl ketone (MEK)), pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Aliphatic and cycloaliphatic ethers (e.g., dichloroethylether, dimethyl ether, MeTHF), saturated and unsaturated aliphatic or aromatic hydrocarbons (decane, toluene, benzene, cymene, 1-methyl naphthalene), oxygenated hydrocarbons (e.g. furan, nonyl phenol, etc.), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like). Lignin derived solvents such as Guaiacol, Eugenol, 2-Methoxy-4-propylphenol (MPP), 2-Methoxy-4MethylPhenol (MMP) or mixture thereof may also be used. Combination of solvents may also be used to fine tune the extracting capability of the solvent.

Preferably, the organic solvent or the combination of organic solvents can extract 80 mol % or more of the furfural produced from the aqueous phase, while at the same time dissolve less than 1 wt %, even preferably less than 0.1 wt %, still more preferably less than 0.01 w %. of water.

The weight percentage of organic phase material is in a range suitable to create a biphasic system with the aqueous phase, e.g., from about 5% by weight to about 95% by weight, based on the combined weight of the aqueous phase and organic phase.

The dehydration process step 300 is carried out for a period of time (residence time) ranging from about 1 minute to about 24 hrs, preferably for a period of time ranging of from about 5 minutes to about 12 hrs, more preferably from about 10 minutes to about 6 hours, still more preferably 30 minutes to 4 hrs., even still more preferably 30 minutes to 2 hrs. or for times within these ranges, at an elevated temperature above about 100° C., including in the range from about 100° C. to about 250° C., from about 110° C. to 200° C. and from about 140° C. to about 180° C. One or more dehydration acids as described above may be used in the dehydration step in order to catalyze the reaction process. The pressure is preferably autogenous pressure of hot steam.

The concentration of the C5-carbohydrate compounds in the dehydration reactor 300 can vary depending upon the product to be obtained. However, in accordance with aspects of the present invention, it has been found that the reaction is optimized for obtaining furfural or other furfural derivatives when the concentration of C5 components during the dehydration process step 300 is between about 0.1 wt % and 20 wt %, more preferably between about 0.2 wt % and 10 wt %, inclusive %, based on the weight of the aqueous phase.

During the dehydration process step, at least part, and preferably substantially all, of the C5-carbohydrate compounds are converted to furfural. Optionally, other furfural derivatives may also be formed. Due to the nature of the furfural, and optional other furfural derivatives, the furfural preferably reside in the organic phase of the biphasic mixture. Due to the preference of the formed furfural to reside in the organic phase in rather than in the aqueous phase at least part of the formed furfural, and preferably more than 50 wt %, still more preferably 75 wt % of the formed furfural will dissolve in the organic phase.

Following the dehydration step 300, dehydration product stream 310 is transferred to an extractor (preferably liquid-liquid extractor) for the extraction step 330, optionally after cooling of the stream. The dehydration product comprises at least part of the biphasic mixture, comprising an aqueous phase and a water-immiscible organic phase, which was present in the reaction vessel during the dehydration process and thus comprises water, organic solvent and further comprises furfural that was formed by the dehydration of the C5-carbohydrates. The furfural, herein will be predominantly dissolved in the organic solvent.

The extraction 330 can be operated at a temperature range from about room temperature to about the dehydration temperature, so long as the liquid separates into two liquid phases at the extractor temperature. The organic phase is separated from the aqueous phase, and thus obtained aqueous recycle stream 318 may be fed directly back into the process loop to the hydrolysis reaction step. Depending upon the salt, and optional other organic byproduct, content of the aqueous stream, aqueous recycle stream 318 may be treated to remove unwanted or excessive amounts of salts and/or organic byproducts. Preferably, aqueous recycle stream is subjected to a separation step (not shown). The recovered aqueous recycle stream obtained after treatment of aqueous recycle stream, is reintroduced to the hydrolysis reaction step 114. Salts, and optionally other organic byproducts like humins, are formed as a byproduct during one or more of the process steps. Typically, part of stream 318 may also be purged from the process to prevent the build-up of byproducts as part of separation step.

Prior to undergoing the liquid-liquid extraction step, dehydration product stream 330 may optionally be routed through a, preferably solid/liquid, separation step, to remove any insoluble humins or other tar that may have been formed during the dehydration step 300, and which may otherwise negatively interfere with the separation of the organic phase from the aqueous phase, or later separation or purification steps (not shown). The humins or tar will predominantly end up in the solid phase and will thus not, or to a lesser extent, affect the subsequent organic/aqueous separation step 330. Formation of tar, char, and/or humins is a well known problem associated with the production of bio-based products, and their non removal from the production stream can result in problems during downstream purification and/or separation steps.

The organic phase, i.e. the organic solvent, is retrieved from extraction step 330 as organic product stream 350, containing the target organic compounds such as furfural and furfural derivatives. Although, part of organic product stream may be recycled to dehydration reactor 300, the majority of organic product stream 350 is subjected to a separation step, preferably one or more distillation steps, in separation zone 400. Residual water from the reaction that was not removed during the liquid-liquid extraction step, and which may contain acetic acid or other water-soluble impurities, is removed via flow stream from separation zone 400, with recovery of furfural via stream 420.

Organic solvents 410 removed/recovered during the separation in separation zone 400 step can be recycled back into the process, such as by reintroduction back into the dehydration reaction vessel 300, in order to minimize production costs and maintain the reaction process and process efficiency. Alternatively, at least part of the organic solvent stream 410 can be directed to a further solvent purification process such as column distillation/separation or solvent-solvent extraction (not shown), prior to reintroduction back into the production process, so as to remove impurities, primarily humins (heavy byproducts), as well as purify the solvent before reintroduction. After the solvent purification step, fresh solvent may be added to the purified solvent stream prior to reintroduction to the dehydration reaction vessel so as to maintain the required volume of organic phase in the dehydration step.

Wet solids stream 220 may still contain substantial amounts of residual C5-carbohydrates. In order to extract any residual C5 carbohydrates, the wet solids stream are preferably, washed with at least part of aqueous stream 318 (not shown) prior to providing the aqueous stream to the hydrolysis system 114.

In a particular embodiment of the process according to the invention the wet solids stream 220 may be further treated to produce alcohols and glycols. The solids comprising cellulose contained in wet solids stream 220, once separated from the C5-carbohydrate-containing liquid process stream 210 as discussed in detail above, can be subjected to a variety of processes. It is contemplated that the wet solids containing cellulose in the wet solids stream 220 (and products separated therefrom) can be separated out as pulp for use in the paper product industry, and can also be used to generate biomass-derived alcohols, biomass derived mono- and diacids, biomass-derived (polymeric) polyols, biomass-derived diols, power, and other chemicals useful in industrial manufacturing operations. As explained in more detail herein below, the solids containing cellulose may be used to from alcohols such as butanol/ethanol or butanediol, e.g. via hydrolysis and fermentation. Glycols like ethylene glycol and propylene glycol may be produced via hydrolysis of the C6 sugars, but may alternatively be produced by a catalytic conversion of the C6 sugars to diols. The cellulose can also be converted to mono- and diacids such as acetic acid, lactic acid, levulinic acid or succinic acid by means of fermentation or chemical conversion.

The solids may also be used to generate power by burning the wet solid residue e.g. in a in co-generation boiler. Alternatively, the wet solid product stream may be converted and optionally dried to form pellets, which can be used to produce for instance power at remote locations.

Exemplary biomass-derived diols include, but are not limited to, $C_2$-$C_{10}$ diols such as ethylene glycol, propylene glycol, 1,4-butane diol (BDO), pentane diol, propylene glycol, 1,2-propanediol, 1,3-propanediol, 1,5-pentanediol, 1,4-pentanediol, 1,2-butanediol, 1,3-butanediol, 2,3-butanediol, 1,4-butanediol 1,2-pentanediol, 1,3-pentanediol, 1,4-pentanediol, 1,5-pentanediol, 2,3-pentanediol, 2,4-pentanediol, and combinations thereof.

Exemplary chemicals that can be produced from the production steps detailed herein include butanol (both n-butanol and iso-butanol), butanol mixes, HMF (hydroxymethyl)furfural and MMF (5-methoxymethyl furfural).

Additionally, the solids removed during various steps of the process described herein may be converted to power or energy, such as by burning or otherwise treating the solids in a power plant or similar power production facility, the power being storable for later sale, or used to fuel the closed-loop process, thereby increasing the process efficiency. The solid tar and/or humins can also be converted to a fuel gas, such as by gasification methods to produce low tar fuel gas with low emissions and no toxic waste streams or burned as fuel in a boiler.

The residual α-hydroxysulfonic acid can be removed by application of heat and/or vacuum from carbohydrate containing product stream to reverse the formation of α-hydroxysulfonic acid to its starting material to produce a stream containing fermentable sugar substantially free of the α-hydroxysulfonic acid. In particular, the product stream is substantially free of α-hydroxysulfonic acid, meaning no more than about 2 wt % is present in the product stream, preferably no more than about 1 wt %, more preferably no more than about 0.2 wt %, most preferably no more than about 0.1 wt % present in the product stream. The temperature and pressure will depend on the particular α-hydroxysulfonic acid used and minimization of temperatures employed are desirable to preserve the sugars obtain in treatment reactions. Typically the removal may be conducted at temperatures in the range from about 50° C., preferably from about 80° C., more preferably from 90° C., to about 110° C., up to about 150° C. The pressure should be such that the α-hydroxysulfonic acid is flashed in its component form at the temperature for removal of the acid. This pressure should be at or above the pressure of the saturated steam at such temperature but low enough to flash the α-hydroxysulfonic acid in its component form. For example, the pressure may be in the range of from about 0.1 bara, to about 5 bara, more preferably from 0.5 bara to about 2 bara. It can be appreciated by a person skill in the art that the treatment reaction 114 and the removal of the acid 120 can occurred in the same vessel or a different vessel or in a number of different types of vessels depending on the reactor configuration and staging as long as the system is designed so that the reaction is conducted under condition favorable for the formation and maintenance of the alpha-hydroxysulfonic acid and removal favorable for the reverse reaction (as components). As an example, the reaction in the reactor vessel 114 can be operated at approximately 100° C. and a pressure of 3 bara in the presence of alpha-hydroxyethanesulfonic acid and the removal vessel 120 can be operated at approximately 110° C. and a pressure of 0.5 bara. It is further contemplated that the reversion can be favored by the reactive distillation of the formed alpha-hydroxysulfonic acid. In the recycling of the removed acid, optionally additional carbonyl compounds, $SO_2$, and water may be added as necessary. The removed starting material and/or alpha-hydroxysulfonic acid may be condensed and/or scrubbed by contact with water and recycled to the reaction system 114 as components or in its recombined form.

The preferable residence time of the biomass to contact with the α-hydroxysulfonic acid in the hydrolysis reaction system may be in the range of about 5 minutes to about 4 hours, most preferably about 15 minutes to about 1 hour.

In one embodiment, the cellulose containing product stream can further be hydrolyzed by other methods, for example by enzymes to further hydrolyze the biomass to sugar products containing pentose and hexose (e.g., glucose) and fermented to produce alcohols such as disclosed in US Publication No. 2009/0061490 and U.S. Pat. No. 7,781,191, which disclosures are hereby incorporated by reference.

The term "fermentable sugar" refers to oligosaccharides and monosaccharides that can be used as a carbon source (e.g., pentoses and hexoses) by a microorganism in a fermentation process. In an enzymatic hydrolysis-fermentation processes the pH of the wet solids stream may be adjusted so that it is within a range which is optimal for the cellulase enzymes used. Generally, the pH of the pretreated feedstock is adjusted to within a range of about 3.0 to about 7.0, or any pH there between.

The temperature of the treated feedstock is adjusted so that it is within the optimum range for the activity of the cellulase enzymes. Generally, a temperature of about 15° C. to about 100° C., about 20° C. to about 85° C., about 30° C. to about 70° C. preferably or any temperature there between, is suitable for most cellulase enzymes. The cellulases, β-glucosidase and other accessory enzymes required for cellulose hydrolysis are added to the pretreated feedstock, prior to, during, or after the adjustment of the temperature and pH of the aqueous slurry after pretreatment. Preferably the enzymes are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include cellobiohydrolases (CBH), glucobiohydrolases (GBH), endoglucanases (EG), glycosyl hydrolyase family 61 proteins (GH61) and β-glucosidase. By the term "β-glucosidase", it is meant any enzyme that hydrolyzes the glucose dimer, cellobiose, to glucose. In a non-limiting example, a cellulase mixture may include EG, CBH, GH61 and β-glucosidase enzymes.

The enzymatic hydrolysis may also be carried out in the presence of one or more xylanase enzymes. Examples of xylanase enzymes that may also be used for this purpose and include, for examples, xylanase 1, 2 (Xyn1 and Xyn2) and β-xylosidase, which are typically present in cellulase mixtures.

The process can be carried out with any type of cellulase enzymes, regardless of their source. Non-limiting examples of cellulases which may be used include those obtained from fungi of the genera *Aspergillus, Humicola*, and *Trichoderma, Myceliophthora, Chrysosporium* and from bacteria of the genera *Bacillus, Thermobifida* and *Thermotoga*. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

The cellulase enzyme dosage is chosen to convert the cellulose of the pretreated feedstock to glucose. For example, an appropriate cellulase dosage can be about 1 to about 100 mg enzyme (dry weight) per gram of cellulose.

In practice, the hydrolysis may carried out in a hydrolysis system, which may include a series of hydrolysis reactors. The number of hydrolysis reactors in the system depends on the cost of the reactors, the volume of the aqueous slurry, and other factors. The enzymatic hydrolysis with cellulase enzymes produces an aqueous sugar stream (hydrolyzate) comprising glucose, unconverted cellulose, lignin and other sugar components. The hydrolysis may be carried out in two stages (see U.S. Pat. No. 5,536,325, which is incorporated herein by reference), or may be performed in a single stage.

In the fermentation system, the aqueous sugar stream is then fermented by one or more than one fermentation microorganism to produce a fermentation broth comprising the alcohol fermentation product useful as biofuels. In the fermentation system, any one of a number of known microorganisms (for example, yeasts or bacteria) may be used to convert sugar to ethanol or other alcohol fermentation products. The microorganisms convert sugars, including, but not limited to glucose, mannose and galactose present in the clarified sugar solution to a fermentation product.

Many known microorganisms can be used in the present process to produce the desired alcohol for use in biofuels. Clostridia, *Escherichia coli (E. coli)* and recombinant strains of *E. coli*, genetically modified strain of *Zymomonas mobilis* such as described in US2003/0162271, U.S. Pat. No. 7,741,119 and U.S. Pat. No. 7,741,084 (which disclosures are herein incorporated by reference) are some examples of such bacteria. The microorganisms may further be a yeast or a filamentous fungus of a genus *Saccharomyces, Kluyveromyces, Candida, Pichia, Schizosaccharomyces, Hansenula, Kloeckera, Schwanniomyces, Yarrowia, Aspergillus, Trichoderma, Humicola, Acremonium, Fusarium*, and *Penicillium*. The fermentation may also be performed with recombinant yeast engineered to ferment both hexose and pentose sugars to ethanol. Recombinant yeasts that can ferment one or both of the pentose sugars xylose and arabinose to ethanol are described in U.S. Pat. Nos. 5,789,210, 6,475,768, European Patent EP 1727890, European Patent EPI 863,901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631). It is also contemplated that the fermentation organism may also produce fatty alcohols, for example, as described in WO 2008/119082 and PCT/US07/011923 which disclosure is herein incorporated by reference. In another embodiment, the fermentation may be performed by yeast capable of fermenting predominantly C6 sugars for example by using commercially available strains such as Thermosacc and Superstart.

Preferably, the fermentation is performed at or near the temperature and pH optima of the fermentation microorganism. For example, the temperature may be from about 25° to about 55° C., or any amount there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The fermentation may be conducted in batch, continuous or fed-batch modes, with or without agitation. The fermentation system may employ a series of fermentation reactors.

In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

The fermentation system produces an alcohol stream preferably containing at least one alcohol having 2 to 18 carbon atoms. In the recovery system, when the product to be recovered in the alcohol stream is a distillable alcohol, such as ethanol, the alcohol can be recovered by distillation in a manner known to separate such alcohol from an aqueous stream. If the product to be recovered in the alcohol stream is not a distillable alcohol, such as fatty alcohols, the alcohol can be recovered by removal of alcohols as solids or as oils from the fermentation vessel, thus separating from the aqueous effluent stream. While the invention is susceptible to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

ILLUSTRATIVE EMBODIMENTS

General Methods and Materials

In the examples, the aldehyde or aldehyde precursors were obtained from Sigma-Aldrich Co. α-hydroxyethane sulfonic acid (HESA) was prepared according to US2012/0122152.

Biphasic Dehydration

Biphasic acid dehydration of C5 carbohydrates (primarily xylose) in aqueous streams for examples 3-4 were carried out in a 300 ml Parr batch reactor (Parr Instruments, Inc.). In a typical run, 3 gm of solid acid catalyst is added to a mixture of 100 gm of 5 wt % xylose aqueous solution and 100 gm of an immisicible organic solvent such as Toluene. The reactor was then heated to the reaction temperature of 140° C. and held at that temperature for a residence time of 10 h. After the reaction is complete the reaction mixture were weighed and transferred into a separatory funnel to allow for two liquid phases to separate. After separation, each layer was weighed and analyzed for its content. Aqueous layer was analyzed using HPLC and the Organic layer was analyzed using GC as described below.

Analytical Methods

The aqueous layers from the acid dehydration runs were analyzed and quantified for various components such as glucose, xylose, arabinose, mannose, formic acid, acetic acid, levulinic acid, furfural using high-performance liquid chromatography (HPLC) system (Shimadzu) equipped with a refractive index detector (Shimadzu) on a BIO-RAD 87H Column. Prior to injection, the samples were filtered through 0.45 μm HV filters (Millipore, Bedford, Mass., USA), and a volume of 10 μL was injected. The mobile phase for the column was 5 mM $H_2SO_4$ in Milli-Q water at a flow rate of 0.6 mL/min.

In a typical biphasic dehydration run the furfural concentration in the organic phase or layer was measure using GC. Agilent 6890 GC with a DB-1301 capillary column installed in its split/splitless inlet was used with the FID. The column parameters were 30 m length, 0.25 mm ID, and 1.0 μm film thickness. Method parameters were as follows:

Oven Temp Program—40 C Hold 3 min, Ramp 10 C/min to 280 C Hold 3 min

Inlet Temp 250 C, Injection Volume 1.0 μl, Split ratio 100:1, Constant Pressure 20 psi Helium Carrier gas Detector Temp 325 C, $H_2$ flow 35 ml/min, Air 400 ml/min, and Helium Makeup 25 ml/min Calculations Xylose Conversion={[mole of Xylose]$_{feed}$−[mole of Xylose]$_{AL}$}/[mole of Xylose]$_{feed}$ Furfural Selectivity={[moles of FUR]$_{AL}$+[moles of FUR]$_{OL}$}/{[mole of Xylose]$_{feed}$−[mole of Xylose]$_{AL}$}

Furfural yield=Xylose Conversion*Furfural Selectivity

Where FUR=Furfural, AL=Aqueous layer or phase and OL=organic layer or phase.

Example 1

Hydrolysis with α-hydroxyethane Sulfonic Acid (HESA)—Stream 1

Into a 1 gallon C276 Parr reactor fitted with in situ IR optics was added approximately 350 grams of compositionally characterized corn stover [dry basis: xylan 24% wt.; glucan 33% wt., 16% w moisture] chopped to nominal 0.5 cm particles. To this was added approximately 2600 grams (runs 1-3) and 2200 g (runs 4-6) of 5% wt. α-hydroxyethane sulfonic acid (HESA) prepared by the dilution of a 40% wt. stock solution of the acid, acid recycled from vaporization of components at the end of a reaction cycle, excessive pressate liquid from the bottoms after pressing the un-dissolved to about 20-22% w. Runs 1-3 targeted about 11% w fresh dry corn stover to begin a run, while runs 4-6 targeted about 13% w. Target concentration of acid was confirmed by proton NMR of the starting mixture integrating over the peaks for water and the acid. The reactor top with a 4 blade down pitch impeller was placed on top of the reaction vessel and the reactor sealed. The pressure integrity of the reactor system and air atmosphere replacement was accomplished by pressurization with nitrogen to 100 psig where the sealed reactor was held for 15 minutes without loss of pressure followed by venting to atmospheric pressure. IR acquisition was initiated and the reaction mixture stirred at 500 rpm. The reactor was then heated to 120° C. and held at target temperature for 60 minutes. During this period of time the in situ IR reveals the presence of HESA, $SO_2$, and acetaldehyde in an equilibrium mixture. An increase in sugars is evident in the IR spectra, with an increase in the band height typical of xylose and glucose being apparent. At the end of the reaction period the acid reversal was accomplished via opening the gas cap of the reactor to an overhead condensation system for recovery of the acid and simultaneously adjusting the reactor temperature set point to 100° C. Vaporization from the reactor quickly cools the reactor contents to the 100° C. set point. The overhead condensation system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with approximately 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of the α-hydroxyethane sulfonic acid. The IR of the overheads revealed that the concentration of the HESA at this point had reached a maximum and then started to decrease due to dilution with condensed water, free of α-hydroxyethane sulfonic acid components, building in the recovery flask. The reaction mixture was then cooled to room temperature, opened and the contents filtered through a Buchner funnel with medium filter paper using a vacuum aspirator to draw the liquid through the funnel. The wet solids are transferred from the Buchner funnel and placed in a filter press where an additional portion of liquid is pressed from the solids to create a high consistency biomass (about 22% w un-dissolved solids) mixture. The dry weight of solid is determined by washing a portion of the solids with water and then oven drying to a constant weight, A small portion of the combined liquid filtrate and pressate is removed for analysis by HPLC, NMR, and elemental analysis via XRF; the remainder is reserved for the next cycle with fresh biomass. A recycle experiment is accomplished by combining the primary filtrate and the pressate liquids with a sufficient quantity of HESA, either recycled from the overheads of the previous run or fresh acid from a 40% wt. stock solution, and water to yield 2200 to 2600 grams of a 5% wt. acid solution which are returned to a 1 gallon C276 Parr reactor where it is mixed with another 350 gram portion of fresh biomass. The pretreatment cycle, venting and recovery, and filtration were repeated five times in addition to the initial starting run to produce the sample used in further experimentation. The HPLC analysis of the pressate is given below in Stream 1 (Table 1).

Example 2

Hydrolysis with α-hydroxyethane Sulfonic Acid (HESA)—Stream 2 and 3

Into a 7 gallon 316 stainless steel batch circulating digester approximately 1820 grams (29.14% w moisture) of compositionally characterized corn stover [dry basis: xylan 17.7% wt.; glucan 33% wt.] chopped to nominal 2 inch particles. A target fresh dry solids to liquids ratio being 9:1 being targeted for each run. The material was placed in a basket and is fixed during the run while liquid is circulated. The solids are removed at the end of the run after a free liquid drain and pressed to remove additional liquid. 1820 g of fresh stover (1290.5 g dry), 1452 g of 40% w of α-hydroxyethane sulfonic acid (HESA) stock solution, 2984 g make-up water, and 7549 g of recycle pressate (make-up water on run 1). The reactor was brought to 120° C. in about 10 minutes and held for 1 hour. The reactor was then vented to remove the bulk of the acid into a caustic scrubber. The acid was not recycled for this study and was made up from the stock solution for each run. Two streams (Stream 2 and 3) generated by this procedure with different xylose concentration were produced and analyzed as given in Table 1.

TABLE 1

Composition of three streams produced using pressure reversible acid digestion of biomass

| | Stream 1 | Stream 2 | Stream 3 |
|---|---|---|---|
| Cellobiose % | n/d | n/d | n/d |
| Sucrose % | n/d | n/d | n/d |
| Glucose % | 1.366 | 0.511 | 1.105 |
| Xylose % | 9.210 | 2.925 | 5.800 |
| Fructose % | n/d | 0.476 | 1.013 |
| Arabinose % | 1.371 | 0.037 | 0.070 |
| Formic % | 0.130 | 0.383 | 0.670 |
| Acetic % | 1.174 | 0.008 | 0.016 |
| HMF % | 0.014 | 0.053 | 0.093 |
| Furfural % | 0.149 | 0.003 | 0.003 |

Example 3

Xylose Acid Dehydration Using Ion Exchange Resin

This acid dehydration run was carried out by adding about 3 gm of Amberlyst® 15 (wet) ion exchange resin catalyst (from Sigma Aldrich) in a 300 ml parr batch reactor as described above to the biphasic mixture. The reaction temperature was 140° C. with a residence time of 10 h. After the analysis of aqueous and organic layers, the xylose conversion was 68% and Furfural selectivity was 47%.

Example 4

Xylose Acid Dehydration Using Amorphous Silica Alumina

This acid dehydration run was carried out by adding about 3 gm of Amorphous SilicaAlumino (ASA) X600 (from CRITERION CATALYSTS & TECHNOLOGIES L.P.) in a 300 ml parr batch reactor as described above to the biphasic mixture. The reaction temperature was 140° C. with a residence time of 10 h. After the analysis of aqueous and organic layers, the xylose conversion was 97% and Furfural selectivity was 37%.

We claim:
1. A method for producing furfural from biomass material containing pentosane comprising:
(a) providing a biomass comprising a polysaccharide containing C5 carbohydrate monomeric units;
(b) contacting the biomass with a solution containing at least one α-hydroxysulfonic acid thereby hydrolyzing the biomass to produce a product stream containing at least one $C_5$-carbohydrate compound in monomeric and/or oligomeric form, and α-hydroxysulfonic acid, the at least one α-hydroxysulfonic acid having the general formula

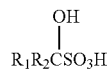

wherein R1 and R2 are individually hydrogen or hydrocarbyl with up to about 9 carbon atoms;
(c) separating at least a portion of the α-hydroxysulfonic acid from the product stream containing at least one $C_5$-carbohydrate compound to provide an acid-removed product stream containing the at least one $C_5$-carbohydrate compound and recovering the α-hydroxysulfonic acid in its component form;
(d) separating a liquid stream containing said at least one $C_5$-carbohydrate compound and a wet solid stream containing remaining biomass from the acid-removed product;
(e) dehydrating the $C_5$-carbohydrate compound in at least a first portion of the liquid stream in the presence of a heterogenous solid acid catalyst capable of catalyzing the dehydration of C5 carbohydrates to furfural and/or its derivatives, in a biphasic reaction medium comprising an aqueous phase and a water-immiscible organic phase, at a temperature in the range of from about 100° C. to about 250° C.;
(f) separating an organic phase stream containing furfural and an aqueous stream from the dehydration product stream;
(g) recycling at least a portion of the aqueous stream or a second portion of the liquid stream to step (b);
(h) recovering furfural from the organic phase stream.

2. The method of claim 1 wherein the solid acid catalyst is a solid acid catalyst having total acid site strength higher than 0.05 mmol/g.

3. The method of claim 1 wherein the dehydration step is carried out at a temperature in the range of from about 140° C. to about 250° C.

4. The method of claim 1 wherein at least a second portion of the liquid stream from step (d) is recycled to step (b).

5. The method of claim 1 wherein at least a portion of the aqueous stream from step (f) is recycled to step (b).

6. The method of claim 1 wherein at least a portion of the aqueous stream from step (f) and a second portion of the liquid stream from step (d) are recycled to step (b).

7. The method of claim 1 wherein at least a portion of the organic phase stream after recovery of furfural is recycled to step (e) to provide the biphasic reaction medium.

8. The method of claim 7 wherein the organic phase stream after recovery of furfural is purified prior to recycling to step (e).

9. The method of claim 2 wherein the contact time of the first portion of the liquid stream to the heterogenous solid catalyst is in the range of 1 minute to 24 hours.

10. The method of claim 1 wherein step (b) is carried out at a temperature within the range of about 50° C. to about 150° C. and a pressure within the range of 0.1 bara to about 11 bara.

11. The method of claim 1 wherein the solid acid catalyst is selected from the group consisting of acidic ion exchange resins, acidic zeolites, layered clay, amorphous silica alumina, gamma alumina, mesoporous silicate and aluminosilicates, aluminum incorporated mesoporous silica, sulfonic acid functionalized metal oxides, and microporous silicoaluminophasphates, perfluorinated ion-exchange materials, sulfonated grapheme oxide, and heteropolyacids.

12. The method of claim 11 wherein the solid acid catalyst is selected from the group consisting of acidic ion exchange resins, acidic zeolites, amorphous silica alumina, and mesoporous silicate and aluminosilicates.

13. The method of claim 12 wherein the solid acid catalyst is acidic ion exchange resin.

14. The process of claim 1, wherein the liquid stream separated from the wet solid stream comprises C5 carbohydrates in a concentration ranging from about 0.1 wt % to about 15 wt %.

15. The method of claim 1 wherein mineral acid is added to step (b) or step (c).

16. The method of claim 7 wherein the separation in step (c) is carried out at a temperature within the range from about 50° C. to about 150° C. and a pressure within the range from about 0.1 bara to about 5 bara.

17. The method of claim 1 wherein at least a portion of the aqueous stream from step (f) is contacted with the wet solid stream prior to recycling to step (b).

18. The method of claim 1 wherein the α-hydroxysulfonic acid is present in an amount of from about 1% wt. to about 55% wt., based on the solution.

19. The method of claim 1 wherein the α-hydroxysulfonic acid is produced from (a) a carbonyl compound or a precursor to a carbonyl compound having the general formula

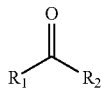

where R1 and R2 are individually hydrogen or hydrocarbyl with up to about 9 carbon atoms or a mixture thereof with (b) sulfur dioxide or a precursor to sulfur dioxide and (c) water.

20. The method of claim 1 wherein the α-hydroxysulfonic acid is in-situ generated.

* * * * *